United States Patent
Becker et al.

(10) Patent No.: US 6,402,915 B1
(45) Date of Patent: *Jun. 11, 2002

(54) RUNNING TANK ASSEMBLY FOR ELECTROPHORESIS

(75) Inventors: Robert G. Becker, Northridge; Richard T. L. Chan, La Jolla; Min Kar Moi, San Diego, all of CA (US)

(73) Assignee: C.C. IMEX, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/354,292

(22) Filed: Jul. 15, 1999

Related U.S. Application Data

(63) Continuation-in-part of application No. 09/079,342, filed on May 15, 1998, now Pat. No. 6,063,250.

(51) Int. Cl.[7] .................... G01N 27/26; G01N 27/447
(52) U.S. Cl. .................. 204/466; 204/456; 204/606; 204/616
(58) Field of Search ................. 204/456, 466, 204/467, 470, 606, 616, 618, 619, 620

(56) References Cited

U.S. PATENT DOCUMENTS

| | | | | |
|---|---|---|---|---|
| 3,616,456 A | | 10/1971 | Valmet | 204/644 |
| 3,839,184 A | | 10/1974 | Richter | 204/600 |
| 3,873,433 A | | 3/1975 | Seidel et al. | 204/462 |
| 4,164,464 A | | 8/1979 | Allington et al. | 204/600 |
| 4,310,408 A | | 1/1982 | Rose et al. | 204/600 |
| 4,415,426 A | | 11/1983 | Hsu et al. | 204/674 |
| 4,576,702 A | | 3/1986 | Peck et al. | 204/613 |
| 4,752,372 A | | 6/1988 | Rhodes et al. | 204/450 |
| 5,045,172 A | * | 9/1991 | Guzman | 204/452 |
| B14,164,464 A | | 5/1992 | Allignton et al. | 204/600 |
| 5,405,520 A | | 4/1995 | Helfer | 204/606 |
| 5,407,552 A | | 4/1995 | Lebacq | 204/619 |
| 5,449,446 A | * | 9/1995 | Verma et al. | 204/612 |
| 5,582,702 A | | 12/1996 | Cabilly et al. | 204/456 |
| 6,063,250 A | * | 5/2000 | Becker | 204/450 |

OTHER PUBLICATIONS

Brochure: Mupid–21 Mini–Gel Electrophoresis Unit–For DNA, RNA, & Proteins. Cosmo Bio Co., Ltd., Tokyo, Japan. 1997.

* cited by examiner

*Primary Examiner*—Jill Warden
*Assistant Examiner*—John S. Starsiak, Jr.
(74) *Attorney, Agent, or Firm*—John L. Rogitz

(57) ABSTRACT

An electrophoresis running tank assembly includes a running tank and a power supply holder that is integral to the running tank. A lid is configured for covering the tank, with two activation arms depending downwardly from the lid and with peripheral vertical skirts of the lid overlapping the walls of the tank. Two switches are held by a switch assembly in the power supply holder and are accessible through a space between the power supply holder and a pin wall that supports two connector pins. When the lid is engaged with the tank, the activation arms extend into the space to abut and thereby close the switches, thereby electrically connecting the switches to the electrode. A power supply can be engaged with the pins to energize the electrodes. Owing to the cooperation between the skirts and the walls of the tank, the lid cannot be tilted relative to the tank to expose the electrodes, but instead must deliberately be lifted up and away from the tank (thus opening the switches and deenergizing the electrodes) to expose the electrodes.

17 Claims, 2 Drawing Sheets

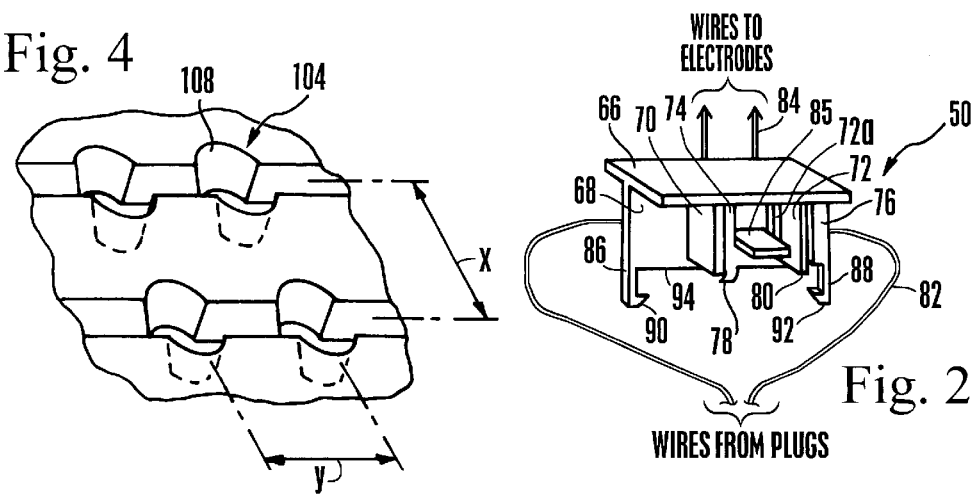
Fig. 4
Fig. 2
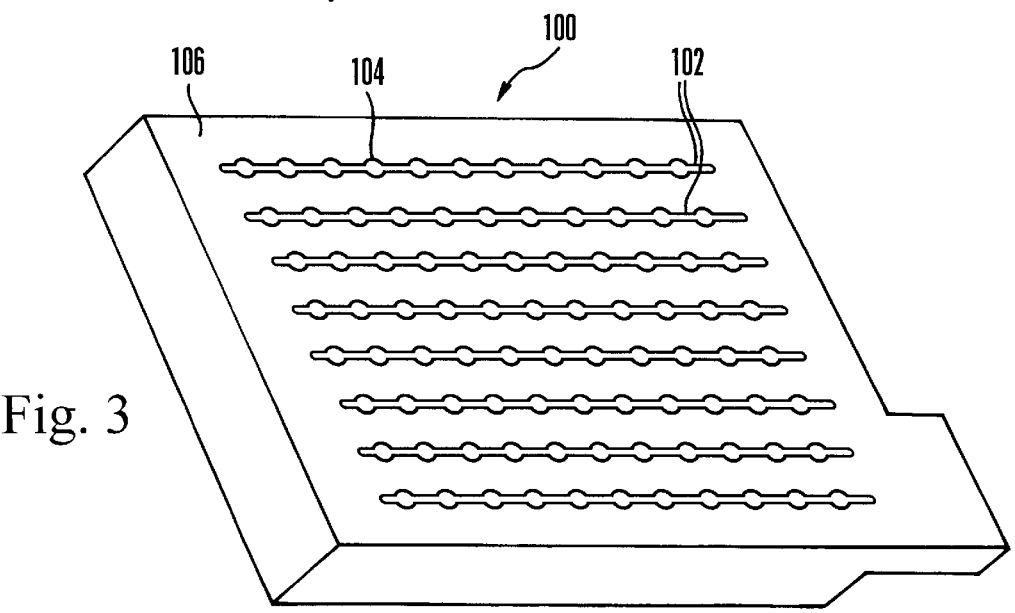
Fig. 3
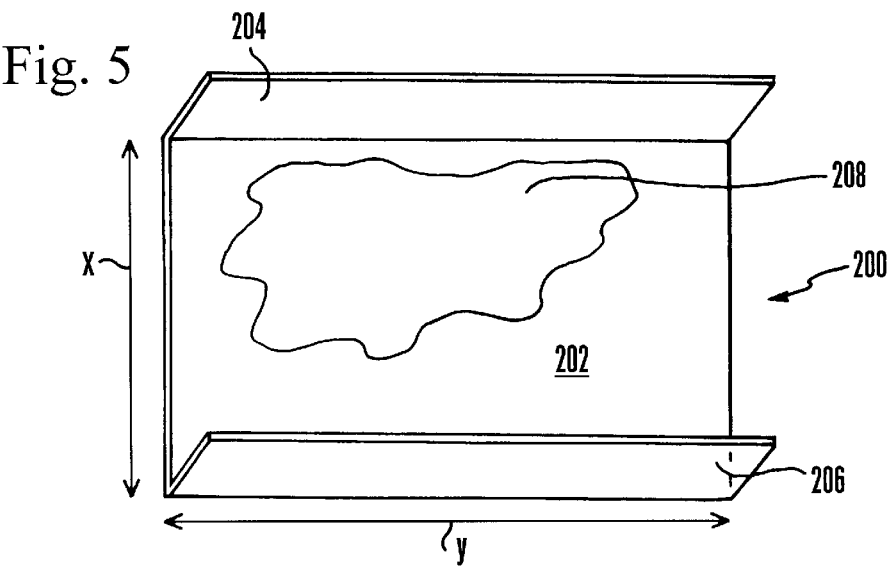
Fig. 5

RUNNING TANK ASSEMBLY FOR ELECTROPHORESIS

This is a continuation-in-part of U.S. patent application Ser. No. 09/079,342, filed May 15, 1998, now U.S. Pat. No. 6,063,250.

FIELD OF THE INVENTION

The present invention relates generally to electrophoresis, and more particularly to running tank assemblies for electrophoresis.

BACKGROUND

Electrophoresis is used for a large number of applications. As an example of but one application, DNA sequencing to determine the genetic composition of a sample of DNA can be undertaken using electrophoresis.

Many existing electrophoresis applications are undertaken using so-called running tanks, in which a sample-containing gel is disposed in an electrophoresis chamber in the tank. Electric current is then applied to the gel by means of an electrode in the tank to cause electrophoresis of the sample.

For safety reasons, the electrophoresis chamber preferably is covered by a lid when energized. To ensure that the lid covers the electrophoresis chamber prior to energizing the gel, interlocks have been provided to break the electric current path between an electrophoresis power supply and the tank electrode when the lid is not properly engaged with the running tank.

As one example of such an interlock, microswitches have been provided on the top edge of running tanks, and the microswitches are closed by a lid when the lid is placed on the tank, thereby completing the electrical circuit between the tank electrode and the power supply. Unfortunately, the tank electrode can be energized anytime the microswitches are depressed, whether by a lid or by a substitute mechanism. Thus, the interlock easily can be defeated.

An alternative interlock is disclosed in U.S. Pat. No. 5,405,520, which discloses a plug that is completely recessed into a running tank cover. The cover is formed with a slot that extends to the plug, and a switch on the running tank is advanced into the slot against the plug when the lid is lowered down onto the tank. When the switch contacts the plug, an electrical circuit is established to the running tank electrode. However, the switch can be "made" by contact with components other than the plug in the cover; consequently, the interlock can be easily defeated.

Still another alternate interlock is exemplified in a device marketed under the trade name "Mupid-21" by Cosmo Bio Ltd. of Japan. In the Mupid-21 device, a running tank cover has a vertical wall and a plug protruding from a front side of the wall. The rear end of the plug is exposed at a rear side of the wall. To engage the lid with a running tank, the lid is lowered onto the tank with the vertical wall of the lid disposed flush against an inside surface of a wall of a power supply bay that is formed as part of the tank. The wall of the power supply bay holds a contact that is connected to the running tank electrode, such that the rear end of the plug wipes the contact when the lid is slid onto the tank. Then, a power supply having a receptacle is advanced into the bay until the plug mates with the receptacle, thereby completing the electrical circuit between the running tank electrode and the power supply.

It happens that a user of an electrophoresis apparatus might undertake many successive electrophoresis experiments over the course of a day, requiring the lid to be removed from the running tank between experiments to modify or replace the gel in the running tank. Unfortunately, the Mupid-21 design necessitates removing the power supply from the bay to remove the lid from the running tank, which users find cumbersome and time consuming. As recognized herein, however, it is possible to provide an electrophoresis running tank assembly which ensures that a power supply cannot be electrically connected to a running tank electrode without first covering the running tank with a lid, and which does not require the power supply to be removed from the assembly to remove the lid from the running tank.

Accordingly, it is an object of the present invention to provide an electrophoresis running tank assembly that addresses one or more of the above-noted problems.

SUMMARY OF THE INVENTION

An electrophoresis running tank assembly includes a tank, at least one electrode disposed in the tank, and a lid configured for covering the tank. In accordance with the present invention, the lid includes at least one activation arm protruding from the lid. At least one switch is provided, preferably recessed in a portion of the assembly, and when the lid is engaged with the tank, the activation arm abuts the switch to close the switch and thereby electrically connect the switch to the electrode.

In a preferred embodiment, the switch is held on the tank, and the lid can be lowered onto the tank to a fully lowered position. The activation arm does not close the switch unless the lid is near or in the fully lowered position. In a particularly preferred embodiment, at least two switches and at least two activation arms are provided.

As disclosed in detail below, a power supply holder is associated with the running tank. The power supply holder defines a power supply bay that is configured for removably receiving a power supply. Also, the power supply holder includes a wall and at least one plug extending from the wall into the bay for engaging the power supply when the power supply is disposed in the bay. Additionally, the power supply holder includes a switch enclosure, with the switch being disposed in the switch enclosure and with the activating arm extending into the switch enclosure when the lid is near or in the fully lowered position to thereby activate the switch.

To prevent tilting the lid to gain access to the electrophoresis chamber of the running tank when the arms of the lid are engaged with the switches (and, hence, when the electrodes potentially are energized), the lid is formed with plural skirts that depend down from the edges of the lid and that overlap the sides of the running tank. With this cooperation of structure, tilting of the lid relative to the running tank (and, potentially, access to energized electrodes) is prevented.

In another aspect, an electrophoresis running tank assembly includes a tank defining plural sides that in turn define respective upper edges. At least one electrode is disposed in the tank. Also, a lid is configured for covering the tank. As set forth in detail below, the preferred lid includes at least one activation arm and defines a top plate that rests on the upper edges when the lid is a fully lowered position. Plural skirts depend downwardly from the top plate, with each skirt overlapping a respective side when the lid is near or in the fully, lowered position to prevent tilting of the lid relative to the running tank. When the lid is engaged with the tank, the activation arm abuts a switch to close the switch and thereby electrically connect the switch to the electrode.

In yet another aspect, a method for electrophoresis includes providing a running tank assembly including a running tank with at least one electrode therein. The method also includes engaging a power supply with the running tank assembly and lowering a lid onto the running tank assembly to cover the running tank. Moreover, the method includes causing a switch to close when the lid is lowered onto the running tank assembly to thereby electrically connect the power supply to the electrode. Tilting of the lid relative to the running tank is prevented when the power supply is electrically connected to the electrode.

The details of the present invention, both as to its structure and operation, can best be understood in reference to the accompanying drawings, in which like reference numerals refer to like parts, and in which:

BRIEF DESCRIPTION OF THE DRAWINGS

FIG. 2 is a perspective view of the switch enclosure removed from the running tank;

FIG. 3 is a perspective view of an alternate lid;

FIG. 4 is a perspective view showing details of the lid shown in FIG. 3; and

FIG. 5 is a perspective view of an extrusion molded gel tray.

DETAILED DESCRIPTION OF THE PREFERRED EMBODIMENT

Figure 1:
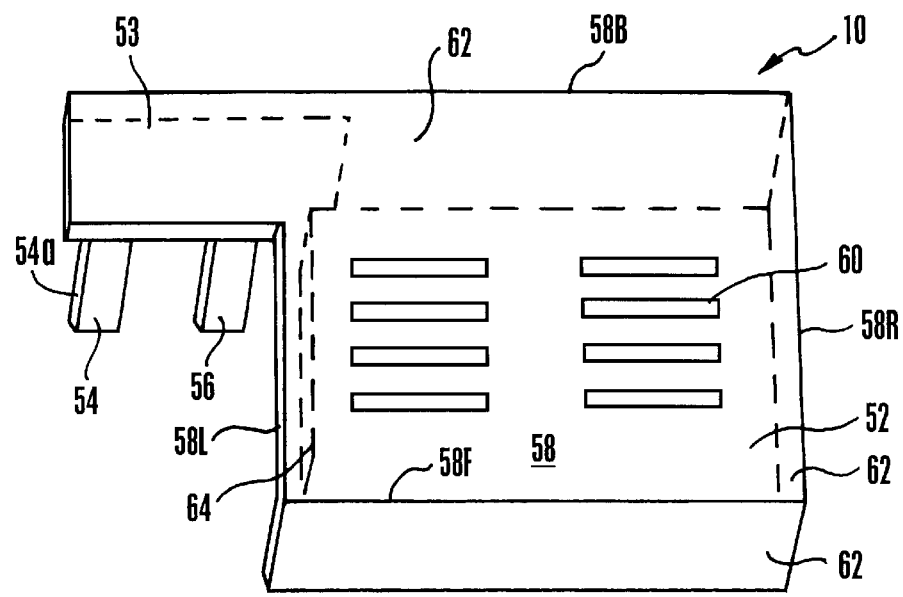
FIG. 1 is a perspective view of the electrophoresis running tank assembly, showing the power supply, running tank, and lid in an exploded relationship, with portions of the lid skirt shown in phantom.
Figure 1:
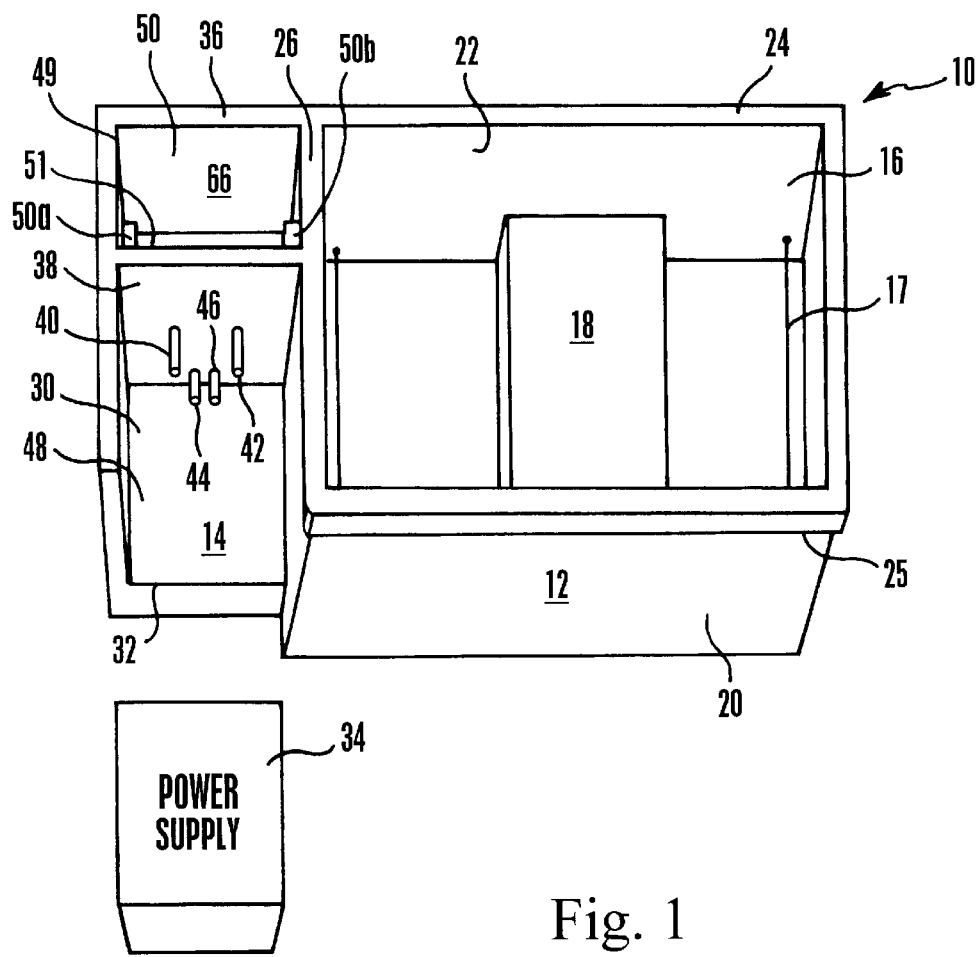

Referring initially to FIG. 1, a running tank assembly for electrophoresis is shown, generally designated 10. It is to be understood that terms of orientation used herein, such as "vertical"and "horizontal", are referenced to the intended upright orientation of the assembly 10 shown in FIG. 1.

As shown, the assembly 10 includes a hollow hard rigid plastic running tank 12 and a hollow plastic power supply holder 14 contiguous thereto. More preferably, the power supply holder 14 is made integrally with the running tank 12. The running tank 12 is configured for electrophoresis, and accordingly the running tank 12 defines one or more electrophoresis chambers 16 in electrical communication with one or more, and preferably two, electrophoresis electrodes 17 preferably configured as wires. A gel containing a sample of, e.g., DNA, can be disposed in the electrophoresis chamber 16 for electrophoresis of the sample in accordance with the present invention. If desired, a central raised ridge 18 can extend longitudinally in the chamber 16 from a front vertical wall 20 of the tank 12 to a rear vertical wall 22. Furthermore, the tank 12 defines a rectangular upper edge 24, and a ledge 25 can extend outwardly from the edge 24 along some or all of the periphery of the edge 24. Likewise, the power supply holder 14 defines an upper edge 26.

Turning more specifically to the power supply holder 14, the holder 14 defines a power supply bay 30, an open front end 32 into which a power supply 34 can be advanced, and a rear vertical wall 36 opposite the open front end 32. A pin wall 38 is disposed intermediate the rear wall 36 and front end 32 as shown, and two horizontally-oriented metal pins 40, 42 are supported by and protrude forwardly from the pin wall 38. The pins 40, 42 engage holes in the power supply 34 when the power supply 34 is appropriately advanced into the bay 30, with the pins 40, 42 being connected to wires or other conductors as set forth more fully below. It is to be understood that the power supply 34 can be energized from an electrical outlet by means of a cord in accordance with conventional principles. If desired, left and right ramps 44, 46 can be formed on the bottom surface 48 of the bay 30 to slidingly receive complementary structure on the bottom of the power supply 34, to guide the power supply 34 into the bay 30.

In accordance with the present invention, a switch assembly 50 is disposed in a switch enclosure 49 that is established between the rear wall 36 and the pin wall 38. An exposed elongated rectangular space 51 of the switch enclosure 49 is established between the switch assembly 50 and the pin wall 38 as shown, with the switch assembly 50 being formed with left and right keyways 50a, 50b for purposes to be shortly disclosed.

A hard plastic, preferably transparent lid 52 can be engaged with the running tank 12 and power supply holder 14 to cover the electrophoresis chamber 16 and to complete the electrical circuit between the pins 40, 42 (and, hence, the power supply 34) and the electrodes 17. In the preferred embodiment, the lid 52 is formed with an arm extension 53, and left and right activation arms 54, 56 depend downwardly from the arm extension 53. The arms 54, 56 are L-shaped in cross-section as can be appreciated in reference to FIG. 1, consequently being formed with respective keys (only the key 54a shown). It can now be appreciated that the arms 54, 56 are received into the space 51 between the switch assembly 50 and the pin wall 38 when the lid 52 is lowered onto the tank 12 (and the arm extension 53 lowered onto the power supply holder 14 to cover the switch assembly 50), with the keys 54a of the arms being received in the keyways 50a, 50b.

With this interlock, insertion of the arms 54, 56 into the space 51 is prevented unless the lid 52 is engaged with the running tank in the proper orientation shown, i.e., covering the running tank. More specifically, when the lid 52 is lowered properly all the way onto the tank (i.e., when a top plate 58 of the lid 52 rests on the top edge 24 of the tank) and the arms 54, 56 consequently are advanced completely into the space 51, each arm 54, 56 moves a respective normally open switch on the switch assembly 50 to a closed position. The switches are in the electrical path between the pins 4D, 42 and the electrodes 17; consequently, the skilled artisan will readily appreciate that the electrodes 17 cannot be energized unless the lid 52 is lowered completely onto the tank in the orientation shown. If desired, trapdoors can be hinged to cover the space 51, with the arms 54, 56 opening the trapdoors as the lid is lowered onto the tank.

As mentioned above, the lid 52 includes a top plate 58. As shown, the top plate 58 is formed with two rows of transversely oriented, elongated viewing slots 60. Each viewing slot 60 is sufficiently small such that a human finger cannot protrude through the slot. On the other hand, the viewing slots permit a person to view the interior of the electrophoresis chamber 16 when the lid 52 is on the tank 12. As recognized herein, conventional running tank lids without slots can become fouled with steam or condensation during electrophoresis, thereby preventing a person from inspecting the chamber 16 during electrophoresis with the lid in place. Owing to the slots 60, the present lid 52 overcomes this drawback. Further, the slots 60 promote heat exchange across the lid 52, so that the temperature of the running buffer advantageously is lower than it would be otherwise.

Plural skirts 62 depend downwardly from respective front, right, and back edges 58F, 58R, 58B of the top plate 58. As intended by the present invention, each skirt 62 overlaps a respective side of the running tank 12 when the lid 52 is near or in the fully lowered position. If desired, a downwardly-depending power supply side flange 64 can extend parallel to the left edge 58L of the lid 52. The cooperation of structure between the sides of the running tank assembly 12 and the skirts 62/flange 64 of the lid 52 prevent tilting of the lid 52 relative to the running tank 12.

By "prevent tilt" is meant that almost all tilt of the lid 52 is prevented when the arms 54, 56 are disposed in the space 51, at least insofar as the lid 52 can't be tilted enough when the, switches are closed to allow a person to insert a finger or pencil or other like object between the lid 52 and tank 12 into the electrophoresis chamber 16 when the electrodes 17 are energized. Instead, the lid 52 must be lifted completely up and away from the tank to expose the chamber 16, in which case the switches on the switch assembly 50 resume their normally open positions to deenergize the electrodes 17 regardless of whether the power supply 34 is engaged with the pins 40, 42.

In other words, the power supply 34 is electrically disconnected from the electrodes 17 when the electrophoresis chamber 16 is uncovered. However, the power supply 34 advantageously need not be removed from the power supply holder 14 to remove the lid 52 from the running tank 12. Indeed, the lid 52 and power supply 34 conveniently can be engaged with the running tank 12 in any order, i.e., lid 52 first or power supply 34 first, with the above-described safety interlock preventing access to an energized electrode 17 in either case.

FIG. 2 illustrates additional details of the switch assembly 50. As shown, the switch assembly defines a horizontal top 66 and a vertical mount wall 68. Two normally open switches 70, 72 are held, by means of threaded fasteners, on respective brackets (only bracket 72a shown in the perspective of FIG. 2). The brackets 72a are formed integrally with the mount wall 68. Thus, the switches 70, 72 are held onto the tank when the switch assembly 50 is engaged with the tank as set forth further below, with the switches 70, 72 thus being recessed into the switch enclosure 49.

The switches 70, 72 can be microswitches or other types of switches. Each switch preferably includes a respective metal pivot leaf 74, 76 that is pivotably mounted on its switch 70, 72 near the top 66 and that is closely spaced from the pin wall 38 when the switch assembly 50 is disposed in the power supply holder 14.

Also, each pivot leaf 74, 76 is formed with a respective lower curved abutment surface 78, 80. When the lid 52 is lowered onto the tank to the fully lowered position, the arms 54, 56 respectively ride against the abutment surfaces 78, 80 to pivot the leaves 74, 76 and thereby close the switches 70, 72. The activation arms 54, 56 do not close the switches 70, 72 unless the lid 52 is near or in the fully lowered position.

A respective power supply side wire 82 is connected to a pin 40, 42 (FIG. 2) and to a first side of the switches 70, 72. On the other hand, a respective electrode side wire 84 is connected to a second side of each switch 70, 72 and to one or more electrodes 17. Accordingly, when the switches 70, 72 are closed by means of lowering the lid 52 onto the tank, the circuit path between the power supply 34 (when it is plugged in to the pins 40, 42) and the electrodes. 17 is completed. If desired, a circuit that uses a single switch with one or plural electrodes can be provided.

If further desired, a flat parallelepiped-shaped shelf 85 can be formed integrally with the wall 68. It is to be understood that the pins 40, 42 extend through the pin wall 38 shown in FIG. 1 into the switch enclosure 49, and that when the switch assembly 50 is engaged as intended, the shelf 85 is disposed just above the portions of the pins 40, 42 that extend into the enclosure 49. This ensures that the pins 40, 42 are not exposed to the user.

In one preferred embodiment, the switch assembly 50 is not made integrally with the power supply holder 14. To hold the switch assembly 50 in the power supply holder, the switch assembly 50 includes two pivotably mounted spring arms 86, 88 formed with respective detents 90, 92. The switch assembly 50 can be lowered into the power supply holder 14 and the detents 90, 92 ride against edges of respective openings (not shown) in the power supply holder 14, pushing the spring arms 86, 88 outwardly. When the detents 90, 92 clear the edges of the openings, the spring arms 86, 88 snap back inwardly under the influence of their material bias to sandwich the bottom surface of the power supply holder 14 between the detents 90, 92 and the bottom edge 94 of the switch assembly 50.

It is to be understood that variations of the particular arm-switch structure shown above are contemplated herein. For example, a lid can be provided having horizontal arms that are slidably engaged with a horizontally-oriented switch recess. Or, the lid of the present invention need not have arms at all, but a bottom plate having upwardly-extending arms can be used to support the running tank, with the arms of the bottom plate extending upwardly into a switch recess to permit electrode energization using present principles. Yet again, the present arms need not be attached to a lid or bottom, but can be provided as separate components that a person would insert into a switch recess to close the switches.

Still further, a sliding switch or switches can be provided on the tank, and when the lid is engaged with the tank, the lid would engage internal mechanisms in the tank to allow the sliding switch to operate, which would simultaneously lock the lid in place so that it could not be removed without turning the sliding switch to the OFF position. The sliding switch would not operate unless the lid was in place. The sliding switch could be replaced by one or more sliding members that would engage with internal switches and would lock the lid in the same way as the sliding switches.

FIGS. 3 and 4 show an alternate lid 100 that is substantially identical in configuration and operation to the lid 52 shown in FIG. 1, with the following exceptions. The lid 100 is formed with a single set of plural elongated grooves 102 for allowing air to pass through the lid 100 into the running tank and for preventing a person from inserting a finger through the grooves 102 into the running tank. In the embodiment shown, the grooves 102 define plural holes 104 that are equally spaced along the length of each groove.

As intended by the present invention, the holes 104 are configured for guiding a pipette tip during sample loading. Specifically, at the top surface 106 of the lid 100 the holes 104 are wider than the grooves 102, and each hole 104 is funnel-shaped in vertical cross-section, as can best be appreciated in reference to FIG. 4. Stated differently, each hole 104 defines a frusto-conical shaped wall 108, with the wall 108 being tapered inwardly from the top surface 106 down.

As shown best in FIG. 4, an x-dimension (i.e., front to back) is defined by the direction between adjacent rows of holes 104, and a y-dimension (i.e., left to right) is defined by the distance between adjacent holes 104 in the same row. The spacing between adjacent rows in the x-dimension can be established as appropriate for matching the rows of wells on a gel sample that might be held within the running tank, whereas the distance between adjacent same-row holes 104 in the y-axis can be established as appropriate for the tip-to-tip spacing on a multichannel pipettor. Or, the orientation of the rows of holes 104 can be orthogonal to that shown in FIG. 3, in which case same-row holes 104 are spaced in the x-axis and the distance between adjacent rows is relative to the y-axis. Under these circumstances, the x-axis spacing is established as appropriate for tip-to-tip spacing of a multichannel pipettor, whereas the y-axis spacing is established as appropriate for matching the rows of wells on a gel sample within the running tank.

FIG. 5 shows an example of an extrusion molded hard plastic tray 200 that can be used to support an electrophoresis gel. The tray 200 has a flat bottom 202 and front and back vertical sides 204, 206, and is configured for holding a gel 208. The x- and y-axes shown in FIG. 5 correspond to those shown in FIG. 4 with respect to the lid of the present invention.

While the particular RUNNING TANK ASSEMBLY FOR ELECTROPHORESIS as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more".

What is claimed is:

1. An electrophoresis running tank assembly, comprising:
   a tank;
   at least one electrode disposed in the tank;
   a lid configured for covering the tank, the lid including at least one activation arm protruding from the lid;
   at least one switch, wherein when the lid is engaged with the tank, the activation arm abuts the switch to close the switch and thereby electrically connect the switch to the electrode, wherein the lid is formed with plural elongated grooves for allowing air to pass through the lid into the running tank and for preventing a person from inserting a finger through the grooves into the running tank.

2. The assembly of claim 1, wherein the switch is held on the tank.

3. The assembly of claim 1, wherein the lid is lowered onto the tank to a fully lowered position, and wherein the activation arm does not close the switch unless the lid is near or in the fully lowered position.

4. The assembly of claim 1, comprising at least two switches and at least two activation arms.

5. The assembly of claim 1, wherein at least some grooves define plural holes configured for guiding a pipette tip during sample loading.

6. The assembly of claim 5, wherein each hole is funnel-shaped in vertical cross-section.

7. An electrophoresis running tank assembly, comprising:
   a tank;
   at least one electrode disposed in the tank;
   a lid configured for covering the tank, the lid including at least one activation arm protruding from the lid;
   at least one switch, wherein when the lid is engaged with the tank, the activation arm actuates the switch to close the switch and thereby electrically connect the switch to the electrode; and
   a power supply holder associated with the running tank, the power supply holder defining a power supply bay configured for receiving a power supply therein, the power supply holder also including at least one plug extending into the bay for engaging the power supply when the power supply is disposed in the bay, the power supply holder further including a switch enclosure, the switch being recessed in the switch enclosure, the activating arm extending into the switch enclosure when the lid is in the fully lowered position.

8. An electrophoresis running tank assembly, comprising:
   a tank;
   at least one electrode disposed in the tank;
   a lid configured for covering the tank, the lid including at least one activation arm;
   at least one switch, wherein when the lid is engaged with the tank, the activation arm actuates the switch to close the switch and thereby electrically connect the switch to the electrode, wherein the tank defines plural sides, the lid defining a top plate resting on the sides when the lid is in the fully lowered position and plural skirts depending downwardly from the top plate, each skirt overlapping a respective side when the lid is in the fully lowered position to prevent tilting of the lid relative to the running tank when the lid is in the fully lowered position.

9. An electrophoresis running tank assembly, comprising:
   a tank defining plural sides;
   at least one electrode disposed in the tank;
   a lid including at least one activation arm, the lid defining a top plate resting on the sides when the lid is in a fully lowered position and plural skirts depending downwardly from the top plate, each skirt overlapping a respective side when the lid is in the fully lowered position to prevent tilting of the lid;
   at least one switch, wherein when the lid is engaged with the tank, the activation arm abuts the switch to close the switch and thereby electrically connect the switch to the electrode; and
   a power supply holder associated with the running tank, the power supply holder defining a power supply bay configured for receiving a power supply therein, the power supply holder also including at least one plug extending into the bay for engaging the power supply at least when the power supply is disposed in the bay, the power supply holder further including a switch enclosure, the switch being disposed in the switch enclosure, the activating arm extending into the switch enclosure at least when the lid is in the fully lowered position.

10. The assembly of claim 9, wherein the switch is held on the tank.

11. The assembly of claim 10, wherein the lid is lowered onto the tank to the fully lowered position, and wherein the activation arm does not close the switch unless the lid is in the fully lowered position.

12. The assembly of claim 11, comprising at least two switches and at least two activation arms.

13. The assembly of claim 9, wherein the lid is formed with plural elongated grooves for allowing air to pass through the lid into the running tank and for preventing a person from inserting a finger through the grooves into the running tank.

14. The assembly of claim 13, wherein at least some grooves define plural holes configured for guiding a pipette tip during sample loading.

15. The assembly of claim 14, wherein each hole is funnel-shaped in vertical cross-section.

16. A method for electrophoresis, comprising the acts of:

provlding a running tank assembly including a running tank with at least one electrode therein, the running tank assembly including at least one switch;

engaging a power supply with the running tank assembly;

engaging a lid with the running tank assembly to cover the running tank;

causing the switch to close when the lid is engaged with the running tank assembly to thereby electrically connect the power supply to the electrode;

preventing tilting of the lid relative to the running tank when the power supply is electrically connected to the electrode, wherein the running tank defines plural sides and the lid defines a top plate engaged with the sides when the lid is in a fully lowered position and plural skirts depending downwardly from the top plate, each skirt overlapping a respective side when the lid is in the fully lowered position to prevent tilting of the lid relative to the running tank when the lid is in the fully lowered position.

17. The method of claim 16, wherein the lid includes at least one downwardly depending arm, and the causing act is undertaken when the arm extends into the running tank assembly to contact the switch.

* * * * *